(12) United States Patent
Agrawal et al.

(10) Patent No.: US 12,017,983 B2
(45) Date of Patent: Jun. 25, 2024

(54) ELECTRICALLY HEATED DEHYDROGENATION PROCESS

(71) Applicant: PURDUE RESEARCH FOUNDATION, West Lafayette, IN (US)

(72) Inventors: Rakesh Agrawal, West Lafayette, IN (US); Zewei Chen, West Lafayette, IN (US); Peter Oladipupo, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 18/169,086

(22) Filed: Feb. 14, 2023

(65) Prior Publication Data
US 2023/0192574 A1     Jun. 22, 2023

Related U.S. Application Data

(63) Continuation of application No. 17/352,632, filed on Jun. 21, 2021, now Pat. No. 11,578,019.

(60) Provisional application No. 63/042,271, filed on Jun. 22, 2020.

(51) Int. Cl.
  *C07C 5/327*       (2006.01)
  *B01J 19/00*       (2006.01)
  *B01J 19/24*       (2006.01)

(52) U.S. Cl.
  CPC ............ *C07C 5/327* (2013.01); *B01J 19/0013* (2013.01); *B01J 19/2415* (2013.01); *B01J 2219/00081* (2013.01); *B01J 2219/00085* (2013.01); *B01J 2219/00132* (2013.01)

(58) Field of Classification Search
  CPC ...... C07C 5/327; C07C 5/333; B01J 19/0013; B01J 19/2415; B01J 2219/00081; B01J 2219/00085; B01J 2219/00132; B01J 6/008
  See application file for complete search history.

(56) References Cited

U.S. PATENT DOCUMENTS

| | | | |
|---|---|---|---|
| 11,578,019 B2 * | 2/2023 | Agrawal | B01J 19/0013 |
| 2022/0119252 A1 * | 4/2022 | Stevenson | B01D 53/047 |
| 2023/0116690 A1 * | 4/2023 | Posselt | B01J 19/2425 252/373 |

* cited by examiner

*Primary Examiner* — Ali Z Fadhel
(74) *Attorney, Agent, or Firm* — Edmonds & Cmaidalka, P.C.

(57) ABSTRACT

Systems and processes for dehydrogenating one or more alkanes using electrically heated dehydrogenation reactors. The source of electric energy or power can be a power grid, solar panel, windmill, hydropower, nuclear power, fuel cell, gas turbines, steam turbines, portable generator or the like. The systems and processes provided herein result in a simpler dehydrogenation process which is particularly beneficial at a small scale and at remote locations, including the well site.

23 Claims, 17 Drawing Sheets

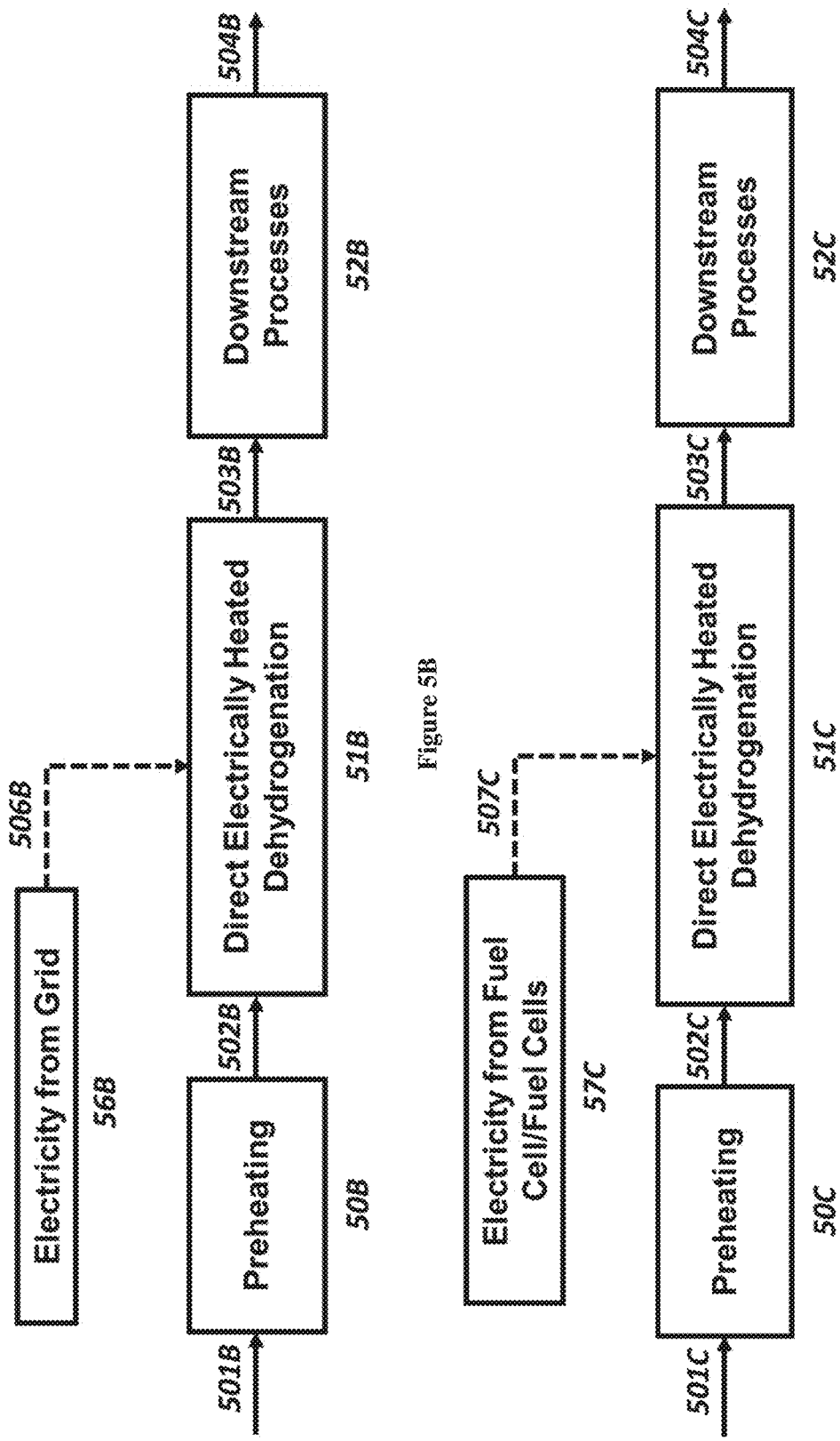

ELECTRICALLY HEATED DEHYDROGENATION PROCESS

CROSS-REFERENCE TO RELATED APPLICATIONS

This application claims priority to U.S. Pat. No. 11,578,019, having application Ser. No. 17/352,632 that was filed on Jun. 21, 2021, which claims priority to U.S. Provisional Patent Application having Ser. No. 63/042,271, filed on Jun. 22, 2020. The entirety of both are incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

Embodiments provided herein relate to systems and processes for dehydrogenation of hydrocarbons or hydrocarbon mixtures. More particularly, embodiments herein relate to systems and processes for dehydrogenation of shale gas mixtures or their individual components.

Description of the Related Art

Recent years, shale gas has become an increasingly important source of natural gas in the United States and it will become even more important in the future. The U.S. government's Energy Information Administration estimates that in 2017 about 62% of the total U.S. dry natural gas production came from shale gas and by 2050, nearly 90% of the United States' natural gas production will come from shale resources. Shale gases contain substantial concentrations of natural gas liquids (NGLs), which are typically separated from methane gas at a natural gas processing plant. NGLs typically consist of $C_2H_6$, $C_3H_8$, $C_4H_{10}$ and $C_5H_{12}$.

Table 1 provides a typical shale gas composition from wells at Barnett, Eagle Ford, and Bakken fields. It is worth noting that $CH_4$ is the predominant component of a shale gas stream (i.e. greater than 50 mol %). The combined mole fraction of all NGL components, $C_2$, $C_3$, $C_4$ and $C_{5+}$ alkanes, in a typical shale gas, generally varies from 5% to 40%.

TABLE 1

Shale Gas Compositions (in mol %) from Wells at Barnett, Eagle Ford, and Bakken fields.

|  | Barnett | Eagle Ford | Bakken |
| --- | --- | --- | --- |
| $CH_4$ | 85 | 74 | 58 |
| $C_2H_6$ | 6 | 14 | 20 |
| $C_3H_8$ | 2 | 5 | 11 |
| $C_4H_{10}$ | 2 | 3 | 4 |
| $C_{5+}$ | 0 | 2 | 1 |
| $N_2$ | 2 | 0 | 4 |
| $H_2O$ | 0.26 | 0.28 | 0.29 |
| $CO_2$ | 2 | 1 | 1 |
| $H_2S$ (mg/scf) | 335 | 307 | 115 |

The typical flowrate from a shale gas well ranges from 1 to 5 MMSCFD (million standard cubic feet per day). Generally, a gas gathering station collects gas from 3 to 10 wells, and the collective flowrates at a gas gathering station can range from 3 to 50 MMSCFD. Gas at a gathering station can be treated to remove acid gas/moisture and sent to a central plant where flowrates are generally in excess of 200 MMSCFD and higher. However, in remote shale gas basins, especially those associated with shale oils, shale gas is directly flared on site, which necessitates a simpler and modular process to covert shale gas into valuable products at a small scale.

FIG. 1 is a block diagram illustrating a conventional steam cracking process wherein hydrocarbons such as ethane and naphtha are cracked or dehydrogenated. When needed, the feed stream 101 is first mixed with steam and preheated in a preheating unit 10 before it is sent to the steam cracking reactor 11. A furnace 14 is used to supply the heat needed for the steam cracker 11. The cracker reactor 11 is also referred to as a dehydrogenation reactor. The stream 103 exiting the cracker 11 is quenched in a quenching tower 12 and then goes through downstream processes 13. This downstream process unit 13 usually contains a series of separation and purification steps to get pure alkene and hydrogen products.

A more detailed representation of the steam cracker 11 is shown in FIG. 2. A typical cracking furnace consists of a radiant section and a convective section. The feed and steam are mixed and preheated to 500 to 650° C. in the convective section. The heated stream is then sent to the radiant section wherein hydrocarbon fuel such as methane and gasoline are burned to produce the heat required for the dehydrogenation reactions. The radiant section houses a set of radiant reactor coils, inside of which the dehydrogenation reactions take place. In the reactor coils, feed coming in at temperatures of 500 to 650° C. are dehydrogenated at temperatures of 750 to 900° C. in 0.1-0.5 seconds. The residence time of the flowing stream within this steam cracker is small, which requires a high heat transfer rate from the furnace to the reactor. To achieve this high heat transfer rate, the reactor coils need to be very thin and yet retain their mechanical strength, which poses a challenge to the coil material. Due to the limitation of the coil material, the temperature difference between the inside and the outside of the reactor is usually above 200° C. to achieve this high heat transfer rate. As a result, up to 42% of the energy obtained from the fuel combustion process can be transferred to the reactor coils in a commercial steam cracking furnace. Hot combustion flue gas leaving the radiant section at around 950 to 1100° C. is then used to preheat incoming feed to the desired reactor inlet temperature as well as to generate steam. The stream out of the steam cracker or the dehydrogenation reactor is quenched to below 600° C. in a transfer line exchanger (TLE) to quickly stop the reaction.

The conventional steam cracking process runs at a large scale in a central plant wherein complex heat recovery networks are designed to recover wasted heat and cut down energy consumption of the process. As shown in FIG. 2, the flue gas out of the radiant section is used to generate steam and preheat the feed to the convective section through multiple heat exchangers. For energy efficiency, the coproduced steam should be put to good use and requires equipment for its processing and handling. Furthermore, these complex heat recovery networks in the convective section are generally not economically feasible in a small scale plant due to limited capital expenditure. Under such circumstance, the fact that only 42% of the energy obtained from the fuel combustion process can be transferred to the reactor coils becomes the bottleneck of the reactor.

Besides the steam cracking reactor itself, the process also requires energy and capital intensive upstream and downstream separations. FIG. 3 shows a typical ethylene production process from shale gas. The sweet and dry shale gas feed in stream 301 is first fed to an NGL recovery unit 30 in which a $CH_4$-rich gas stream 302 is separated from a natural gas liquid stream 303. The $CH_4$-rich gas stream 302 can be sent to any downstream processes or directly to the natural gas pipeline. The natural gas liquid stream 303 goes through a distillation train that includes a deethanizer 31, a depropanizer 32, and a debutanizer 33 wherein ethane 304, propane 305, and butane 306 are separated from the rest of the components sequentially. These distillation columns are generally capital and energy intensive, especially deethanizer and depropanizer wherein cryogenic temperatures are needed. The ethane in stream 304 is sent to the steam cracking reactor 34. The stream 308 out of this reactor contains hydrogen, unreacted ethane, ethylene, and methane, which is a byproduct. The stream 308 out of the steam cracking reactor again goes through a series of separation steps including a $H_2$ separation unit 35, a demethanizer 36, and an ethane/ethylene separation unit 37. This series of separations separates stream 308 into a $H_2$ stream 309, a $CH_4$ stream 310, an ethylene stream 311 and an ethane stream 312. Ethane in stream 312 is recycled back to the steam cracker 34. The propane in stream 305 can also be sent to a catalytic dehydrogenation reactor wherein propane is selectively dehydrogenated into propylene. All these separation units, along with complex reactor design itself, makes the process unlikely to be economical in a small scale plant.

US patent application having application Ser. No. 16/832,092 discloses an alternative process for converting natural gas liquids to alkenes in the absence of steam. Referring to FIG. 4, a mixture of methane and other heavier paraffins 401 is directly sent to a cracker 40 wherein paraffins are cracked. Methane replaces steam as a diluent to lower the paraffin feed partial pressure. The stream 402 out of the cracker 40 can go through a similar separation process as stream 308 in FIG. 3. This process is much simpler than the conventional steam ethane cracking process since the front end separations are not required. Moreover, the equipment related to steam generation, heating, and condensation is also eliminated because there is no steam in the system anymore. Nevertheless, this process is still constrained by the fact that at most 42% of the energy obtained from the fuel combustion process can be transferred to the reactor coils.

There is still a need, therefore, for a simpler and more efficient process for upgrading natural gas liquids, especially in a small scale plant.

SUMMARY OF THE INVENTION

Systems and processes for more efficiently upgrading natural gas liquids are provided. In one embodiment, a process for electrically heated dehydrogenation of hydrocarbons or hydrocarbon mixtures, such as ethane, propane, butanes, naphtha is provided. The feed hydrocarbon mixture can be preheated and fed to an electrically heated dehydrogenation reactor. The flue gas can then be cooled and sent to the downstream processes. The needed electrical power for the dehydrogenation reactor can derive from a grid, solar panel, nuclear power, windmill, hydropower, fuel cell, gas turbine, steam turbine, electric powered generators, gasoline powered generators, diesel powered generators, other portable generators, etc.

In at least one embodiment, the fuel cell is a $H_2$ fuel cell and the $H_2$ is derived from the downstream process or processes. In at least one embodiment, the dehydrogenation reactor is a tube reactor wherein one or more tubes, whether catalyst coated or not, is heated by applying an electric potential (i.e. voltage). In at least one other embodiment, the dehydrogenation reactor is a parallel sheet reactor wherein one or more parallel sheets are heated by applying voltage across them.

In at least one embodiment, the dehydrogenation reactor is a spiral wound reactor wherein the spiral wound is heated by applying voltage across its length. In at least one embodiment, the dehydrogenation reactor is a tube reactor that includes multiple wires of a heating element enclosed in a reactor tube. In at least one embodiment, the dehydrogenation reactor is a tube reactor wherein the heating elements are thin tubes and are enclosed within a high pressure reactor tube. In at least one embodiment, the dehydrogenation reactor is a tube reactor wherein the heating element is used to construct the reactor tube.

Embodiments of the present invention provide a portable solution, in the field, as an alternative to a pipeline or flaring. For example, electric power can be provided to a reactor at the well site. The reactor can be operated using the electric power on site or can be provided by a portable, gasoline or diesel powered, generator. The reactor and any desired separators also can be situated on a truck bed and driven to a location, allowing for dehydrogenation on an as needed or where needed basis, especially when the project economics do not justify the expense for a pipeline. It is also an alternative to flaring a gas cap or shut in well when re-entered for testing, workovers, etc.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

The accompanying drawings are incorporated into and form a part of the specification to illustrate aspects and examples of the present disclosure. These figures together with the description serve to explain the general principles of the disclosure. The figures are only for the purpose of illustrating examples of how the various aspects of the disclosure can be made and used and are not to be construed as limiting the disclosure to only the illustrated and described examples. It is further emphasized that the figures are not necessarily to scale and certain features and certain views of the figures can be shown exaggerated in scale or in schematic for clarity and/or conciseness.

FIG. 5B is a block diagram of an illustrative process where a feed hydrocarbon mixture is preheated and fed to a direct electrically heated dehydrogenation reactor, and the reactor exhaust stream is sent to downstream processes. The needed electricity for the dehydrogenation reactor is from the grid.

FIG. 5C is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from a fuel cell or fuel cells.

DETAILED DESCRIPTION

Figure 1:
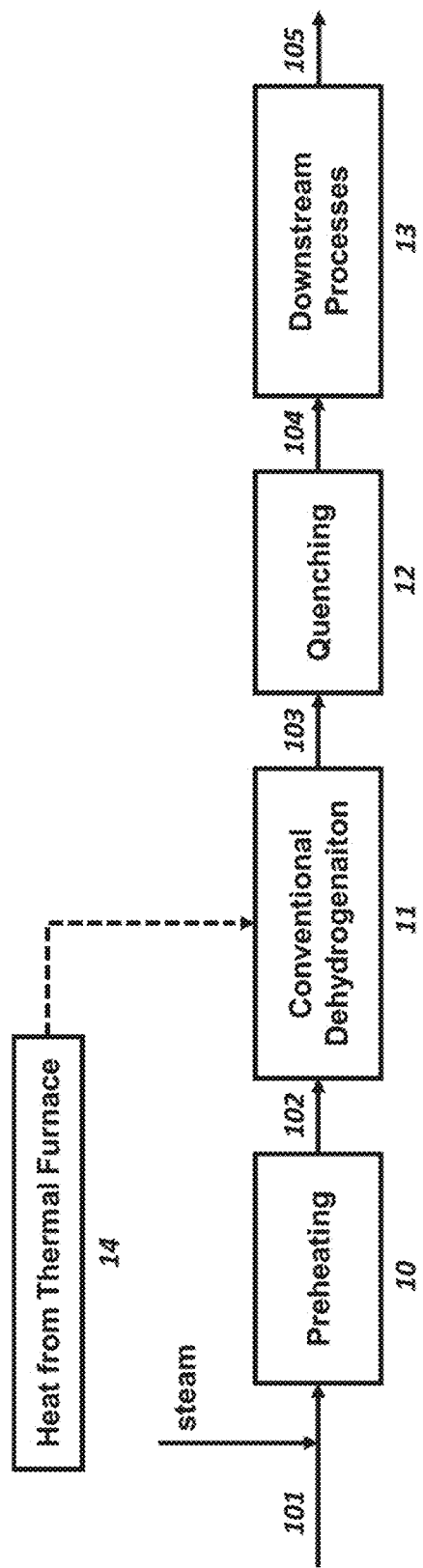
FIG. 1 is a block diagram illustrating the prior art process, wherein the feed hydrocarbon mixture 101 is mixed with stream, preheated and fed 102 to a conventional dehydrogenation reactor, the flue gas 103 is then quenched 104 and sent to the downstream processes to provide a product stream 105. The heat required for the dehydrogenation reactor 11 is from a furnace 14.
Figure 2:
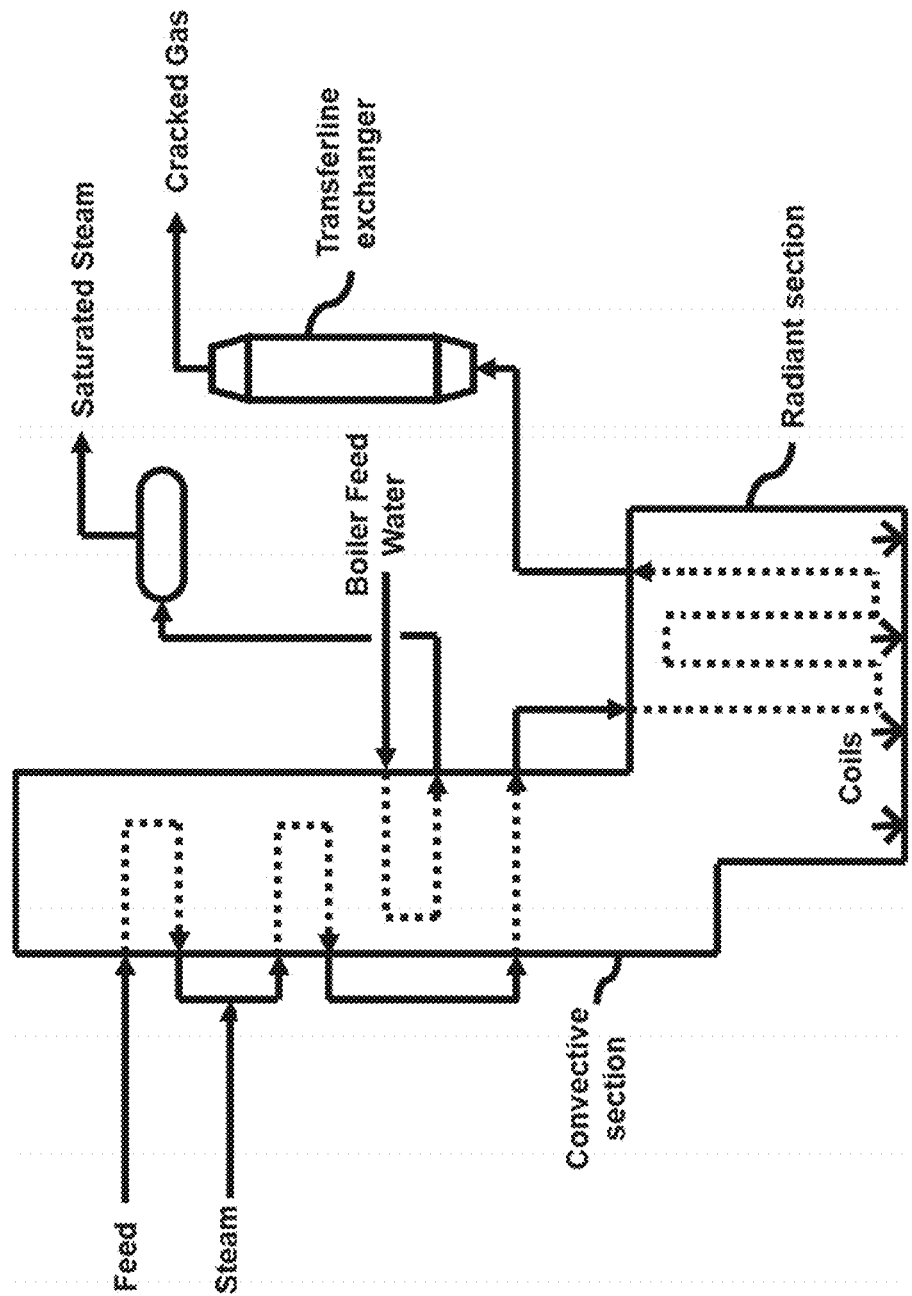
FIG. 2 is a detailed flowsheet of the conventional steam cracking process wherein the feed and steam are mixed, preheated by the flue gas from the furnace, and sent to the steam cracker embedded in a furnace, the steam out of the cracker is then quenched in a transfer line exchanger (TLE).
Figure 3:
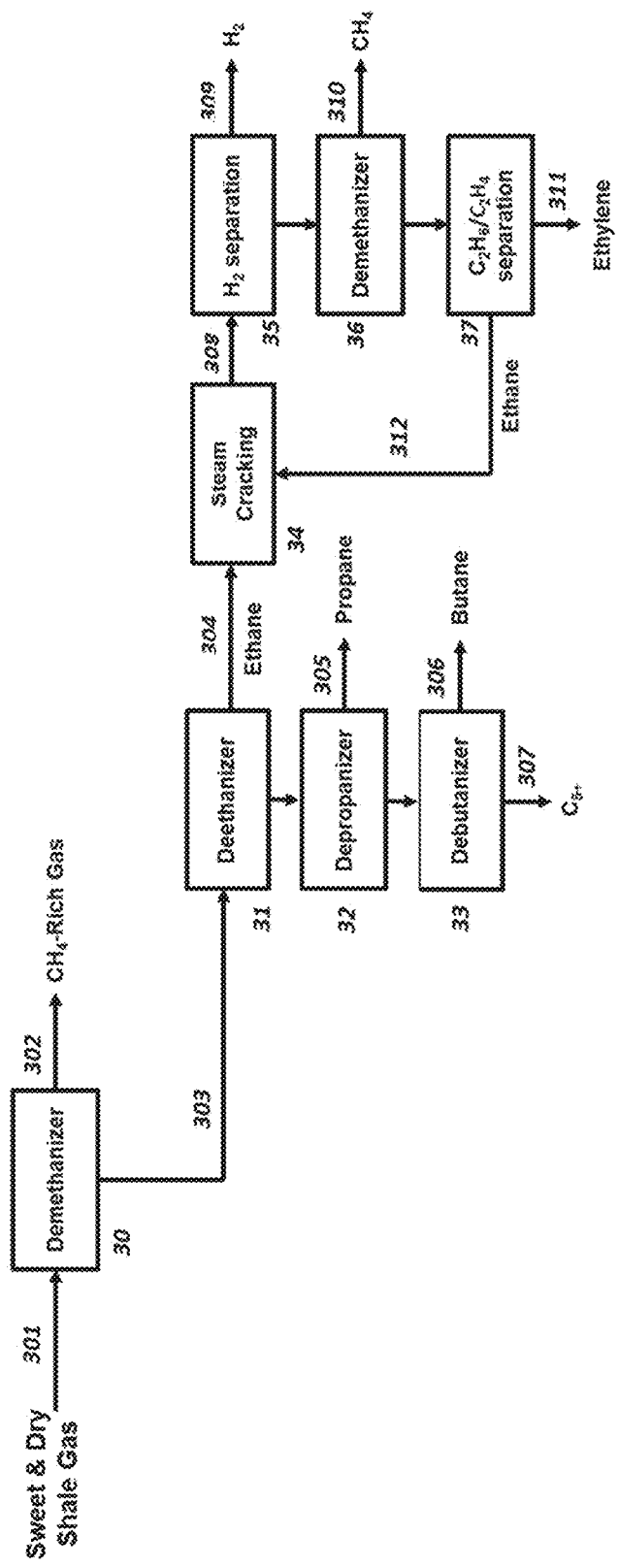
FIG. 3 is a block diagram illustrating a conventional stream cracking process and its associated upstream and downstream separations.

A detailed description will now be provided. It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. The exemplary embodiments presented below also can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function. Furthermore, in the following discussion and in the claims, the terms "including" and "comprising" are used in an open-ended fashion, and thus should be interpreted to mean "including, but not limited to."

The indefinite articles "a" and "an" refer to both singular forms (i.e., "one") and plural referents (i.e., one or more) unless the context clearly dictates otherwise.

The terms "up" and "down"; "upward" and "downward"; "upper" and "lower"; "upwardly" and "downwardly"; "above" and "below"; and other like terms as used herein refer to relative positions to one another and are not intended to denote a particular spatial orientation since the apparatus and methods of using the same can be equally effective at various angles or orientations.

The term "dehydrogenation" refers to a chemical reaction that involves the removal of hydrogen from an organic molecule.

The term "alkane" means saturated compounds containing hydrogen and carbon only, in which all the carbon-carbon bonds are single. The term alkane encompasses linear, branched, and saturated cyclic alkanes.

The terms "alkene" and "olefin" are used interchangeably, and both refer to any unsaturated hydrocarbon containing one or more pairs of carbon atoms linked by a double bond. Such unsaturated hydrocarbons include cyclic or aliphatic olefins, and include mono-olefins, di-olefins, tri-olefins, etc.

The terms "hydrocarbon feed mixture" and "hydrocarbon feed stream" are used interchangeably and both refer to any stream of hydrocarbons that are derived directly from a zone or formation within the earth. Illustrative streams can be or can include a raw shale gas stream or raw natural gas stream or other raw hydrocarbon gaseous stream that is obtained directly (i.e. without processing to remove water and/or acid gas) from a reservoir, wellhead, or pipeline. Illustrative streams can also be or can also include a natural gas stream that is obtained by passing raw natural gas pipelined from a reservoir or wellhead through one or more acid gas removal and dehydration units (i.e. after processing to remove water and/or acid gas). Suitable streams can also originate from a refinery, such as from a FCC, coker, steam cracker, and pyrolysis gasoline (pygas). Suitable streams can also be or can include shale gas, syngas and/or coal gas. For simplicity and ease of description, the detailed description provided herein refers to "shale gas" or "natural gas" or "sweet and dry shale gas" although the embodiments of the present invention equally apply to any hydrocarbon containing at least 5 mol % NGL, regardless of how or where the hydrocarbon is obtained.

The term "or" is intended to encompass both exclusive and inclusive cases, i.e., "A or B" is intended to be synonymous with "at least one of A and B," unless otherwise expressly specified herein.

The term "Ce" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means a hydrocarbon mixture containing Cn and higher hydrocarbons.

The term "raw shale gas" refers to shale gas that is pipelined from reservoirs or wellheads prior to any further processing.

The term "shale gas" refers to natural gas that is produced from a shale or other tight formation, is a gaseous phase mixture containing natural gas liquids, acid gases, water, nitrogen ($N_2$), and possibly trace amounts of contaminants. A suitable shale gas (or natural gas) contains at least 30 mol % $CH_4$ and up to 40 mol % of $C_2H_6$, $C_3H_8$, $C_4H_{10}$, and/or $C_{5+}$ hydrocarbons. For example, a suitable shale gas (or natural gas) contains about 60 mol % to about 95 mol % $CH_4$ and about 5 mol % to about 40 mol % of $C_2H_6$, $C_3H_8$, $C_4H_{10}$, and/or $C_{5+}$ hydrocarbons (or collectively referred to as "$C_{2+}$ hydrocarbons" or "$C_{2+}$ alkanes"). Among the $C_{2+}$ hydrocarbons, $C_2H_6$ is generally the highest concentration followed by $C_3H_8$ then $C_4H_{10}$. Nitrogen gas ($N_2$) can also be present in the shale gas.

The term "sweet and dry shale gas" refers to shale gas obtained after acid gases and water have been removed from the raw shale gas. Insignificant amounts of other components in the sweet shale gas can be removed together with water and thus, a sweet and dry shale gas has almost all the components contained in raw shale gas except acid gases and water. Since acid gases and water can be in relatively small concentration, the composition of the sweet and dry shale gas is similar, or substantially the same, as that of the raw shale gas.

The term "sweet shale gas" refers to shale gas obtained after the acid gases have been removed from the raw shale gas. Insignificant amounts of other components in the raw shale gas can be removed together with acid gases and thus, a sweet shale gas has almost all the components contained in raw shale gas except acid gases.

The term "cracking" refers to a process in which saturated hydrocarbons are broken down into smaller, often unsaturated, hydrocarbons. It is the principal industrial method for producing lighter alkenes (or commonly olefins), including ethene (or ethylene) and propene (or propylene). Steam cracker units are facilities in which a feedstock such as naphtha, liquefied petroleum gas (LPG), ethane, propane or butane is thermally cracked with steam in one or more furnaces to produce lighter hydrocarbons.

The term "fuel cell" refers to an electrochemical cell that converts the chemical energy of a fuel (often hydrogen) and an oxidizing agent (often oxygen) into electricity through a pair of redox reactions.

The terms "grid", "electrical grid", "electric grid" or "power grid" are used interchangeable and all refer to an interconnected network for delivering electricity from power plants to consumers.

The term "steam turbine" refers to a device that extracts thermal energy from pressurized steam and uses it to do mechanical work on a rotating output shaft.

The term "small scale plant" refers to a processing facility or unit that has a process capacity for a shale gas flowrate of less than 200 MMSCFD, preferably 50 MMSCFD and more preferably 30 MMSCFD.

The terms "steam methane reforming" and "SMR" refer to a method for producing syngas (hydrogen and carbon monoxide) by reaction of hydrocarbons with water. Commonly natural gas is the feedstock. The main purpose of this technology is hydrogen production.

The terms "downstream processes" and "downstream processing" are used interchangeably and refer to any one or more processing steps and/or unit operations for quenching, heating, cooling, separation, distillation, sequestration, and/or further reactions including polymerization, alkylation, and oligomerization.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

The following detailed description illustrates embodiments of the present disclosure. These embodiments are described in enough detail to enable a person of ordinary skill in the art to practice these embodiments. It should be understood, however, that the embodiments and examples described herein are given by way of illustration only, and not by way of limitation, the embodiments are chosen and described so that others skilled in the art may appreciate and understand the principles and practices of the present teachings. Various substitutions, modifications, additions, and rearrangements can be made that remain potential applications of the disclosed processes. Therefore, the description that follows is not to be taken as limiting on the scope of the appended claims. In particular, an element associated with a particular embodiment should not be limited to association with that particular embodiment but should be assumed to be capable of association with any embodiment discussed herein.

Figure 5A:
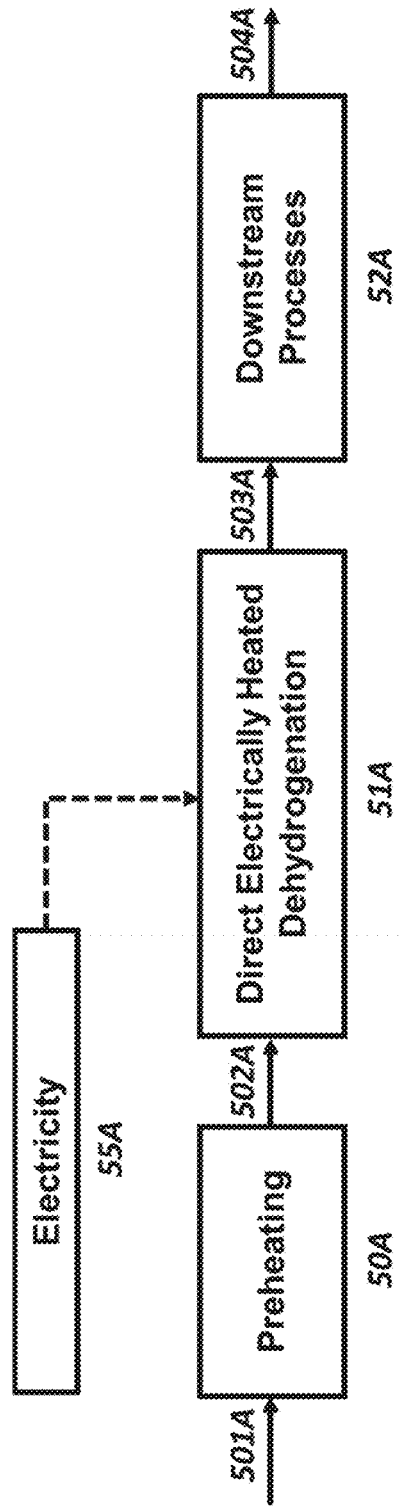
FIG. 5A is a block diagram of an illustrative process where a feed hydrocarbon mixture is preheated and fed to a direct electrically heated dehydrogenation reactor, and the reactor exhaust stream is sent to the downstream processes.

FIG. 5A depicts a flow diagram of an illustrative electrically heated dehydrogenation reactor system. The hydrocarbon feed stream 501A can be preheated to a temperature of 400° C. to 650° C., preferably 500° C. to 600° C. in a preheating unit 50A to provide a gaseous reactant stream 502A. The preheating may be done by any suitable means including heat exchange with a hot process stream available in the plant. This hot process stream may also be obtained from the downstream processes 52A described later and can also be process steam, condensate or other product or process stream at a suitable temperature to provide the requisite heat exchange. The outlet gaseous reactant stream 502A has almost the same composition as the hydrocarbon feed stream 501A and is sent into the electrically heated dehydrogenation reactor 51A, which can be electrically heated from the power source 55A.

The electrically heated dehydrogenation reactor 51A can be operated at 700° C. to 1000° C. and 1 bar to 30 bar. This reactor 51A can be an internal heated reactor wherein the heating alloy is inside the reactor chamber and provides direct heating to the gaseous reactant stream. In the electrically heated dehydrogenation reactor 51A, the hydrocarbon feed stream can be dehydrogenated and cracked into smaller molecules such as hydrogen, methane, ethylene, propylene etc. The outlet stream 503A comprising hydrogen, alkanes, alkenes, aromatics, etc. is then sent to one or more downstream processes, which may include any one or more quenching steps, heat exchangers, separations, further reactions such as polymerization, alkylation, or oligomerization, etc. The final product 504A depends on various decisions for the downstream processes 52A. The electric power 55A to the dehydrogenation reactor can come from a variety of sources, including, but not limiting to a grid, solar panel, windmill, hydropower, nuclear power, fuel cell, gas turbines, steam turbines, electric, gasoline or diesel powered generators, portable generators, etc.

FIGS. 5B-5G depict alternative embodiments utilizing various illustrative electricity sources. The embodiment in FIG. 5B utilizes electricity 506B from the grid 56B. This embodiment results in a simple process without any local facilities to generate electricity for the electrically heated dehydrogenation reactor 51B. The electricity from the grid is usually generated in a gas power plant and the efficiency of a modern combined-cycle gas-fired plants is usually 50%~60%, which is much higher than the efficiency of a furnace. Therefore, embodiments described herein allow for lower energy consumption and carbon footprint comparing to the conventional steam cracking process.

FIG. 5C is another embodiment of the process wherein the electricity 507C for the direct electrified heated dehydrogenation reactor 51C is from a fuel cell or multiple fuel cells 57C. The fuel to the fuel cell could be hydrogen, methanol, or any other suitable fuels. The fuel cell or fuel cells could operate at any temperature between ambient temperature to 1000° C. The pressure of the fuel cell could also be any pressure between ambient pressure to 100 bar. When the fuel cell operates at a high pressure, the flue gas of the fuel cell could be expanded to generate electricity, which can also be used for the direct electrically heated dehydrogenation reactor 51C. This embodiment is beneficial when there is some hydrogen, methanol or other fuel that can be used in a fuel cell available locally.

Figure 5D:
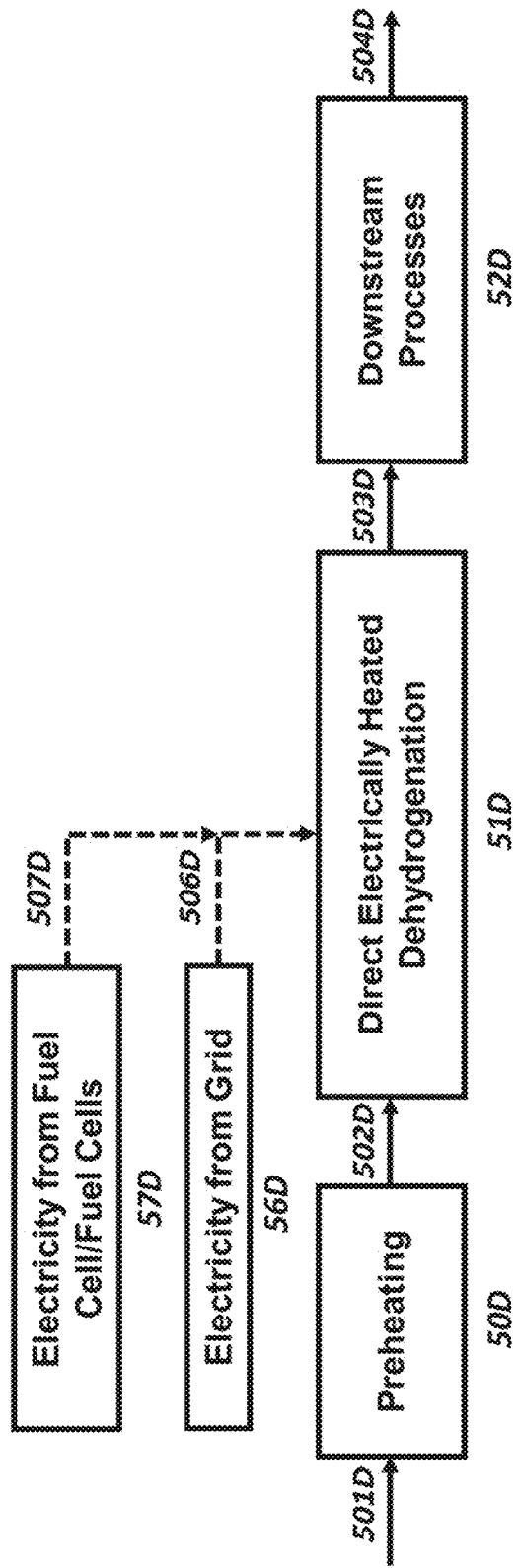
FIG. 5D is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from both a fuel cell or fuel cells and grid.

FIG. 5D is another embodiment in which both the electricity 506D, 507D from the grid 56D and the electricity from the fuel cell/fuel cells 57D are used. The process is beneficial when the available fuel used in the fuel cell is not sufficient to supply all the electricity needed for the dehydrogenation reactor 51D and the shortage will be fulfilled by the electricity from the grid.

Figure 5E:
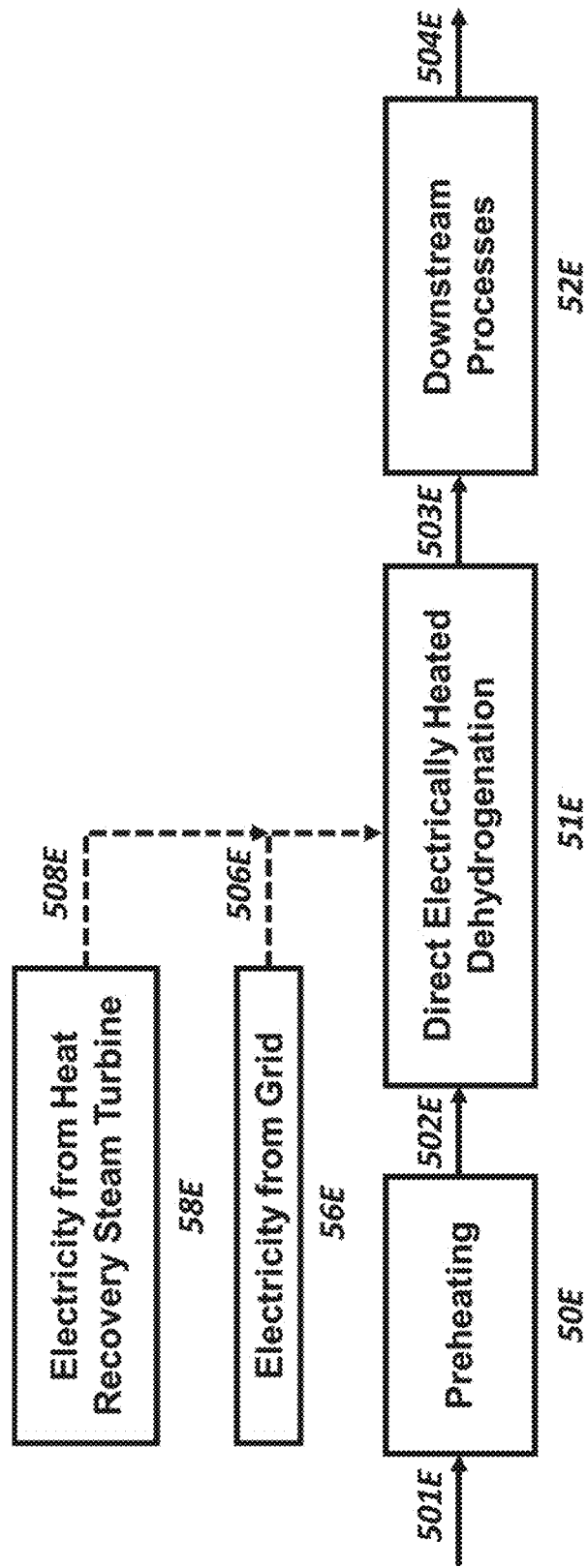
FIG. 5E is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from both grid and a heat recovery steam turbine or heat recovery steam turbines.

FIG. 5E is yet another embodiment in which the electricity 506E, 508E for the direct electrically heated reactor 51E comes from the grid 56E as well as the steam power cycle 58E. The steam power cycle receives heat from various heat sources in the process and generate work through a steam turbine. In this case, any hydrogen produced in the downstream processes 52E can be shipped as a product and no capital investment on the fuel cell is needed.

Figure 5F:
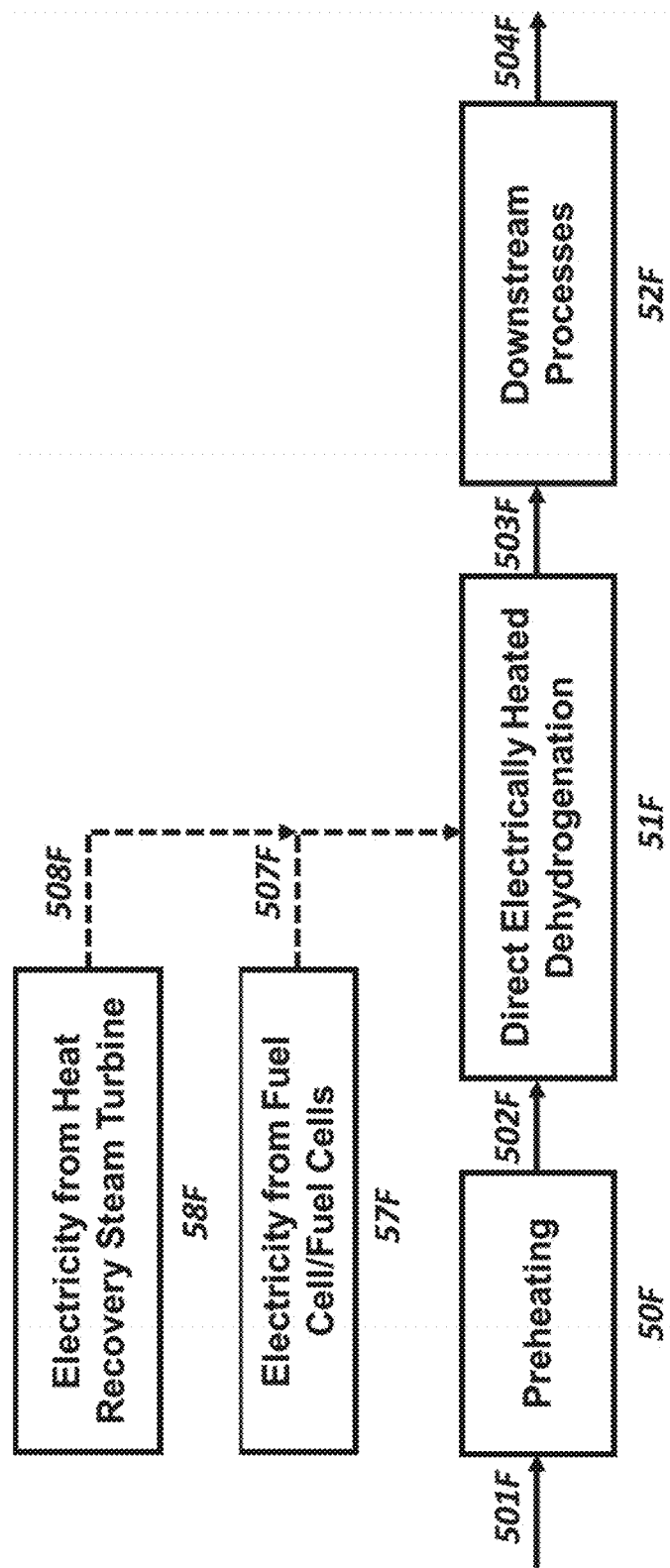
FIG. 5F is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from both a fuel cell or fuel cells and a heat recovery steam turbine or heat recovery steam turbines.

FIG. 5F is yet another embodiment of the invention wherein the electricity 507F, 508F for the direct electrically heated dehydrogenation reactor 51F is from both the steam power cycle 58F and the fuel cell or fuel cells 57F. This process is again beneficial when the available fuel that can be used in the fuel cell is not sufficient to supply all the electricity needed for the dehydrogenation reactor 51F. However, instead of using the electricity from the grid, the electricity from steam recovery turbines is used, which is suitable for the case wherein the plant is located at a remote area and the electricity from the grid is not available.

Figure 5G:
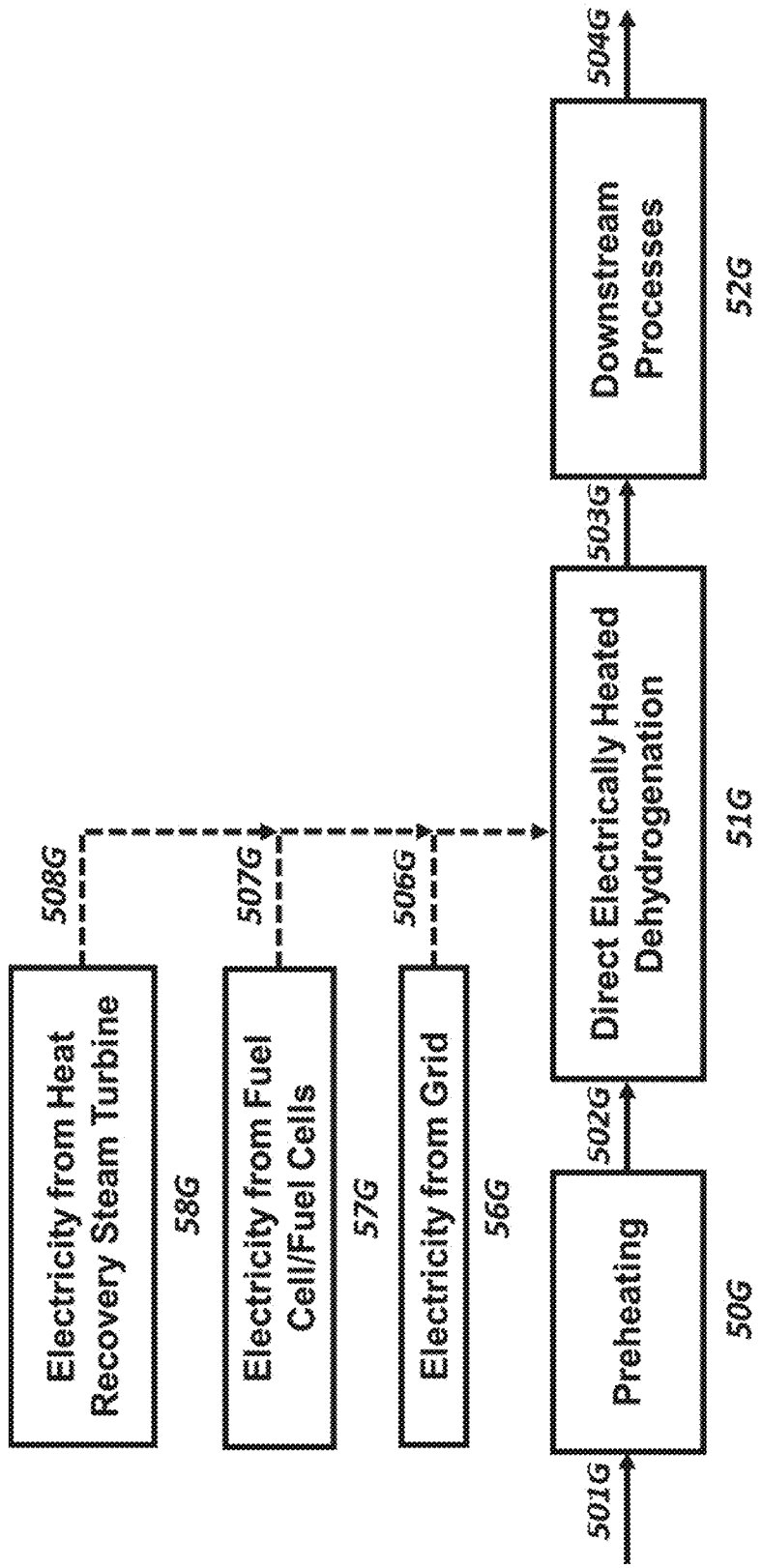
FIG. 5G is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from a fuel cell or fuel cells, a heat recovery steam turbine or heat recovery steam turbines, and grid.

FIG. 5G is yet another embodiment of the invention wherein the electricity 506G, 507G, 508G for the direct electrically heated dehydrogenation reactor 51G is from the grid 56G, the fuel cell or fuel cells 57G, and the steam power cycle 58G.

Figure 6A:
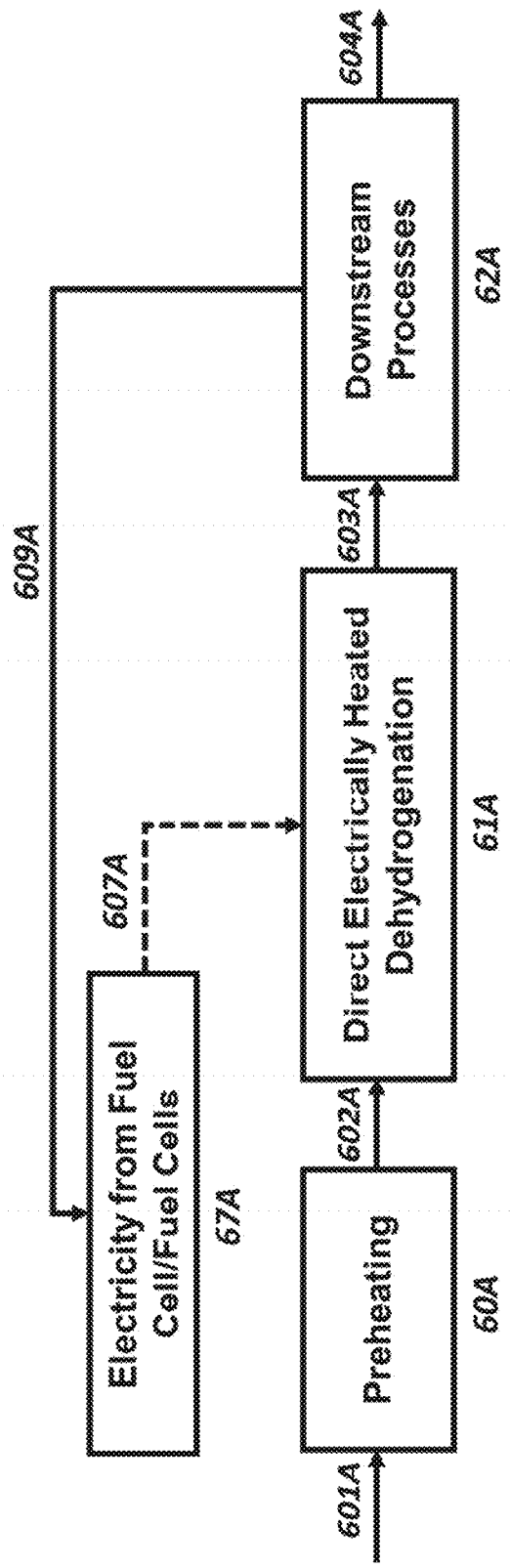
FIG. 6A is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from a hydrogen fuel cell or hydrogen fuel cells wherein the hydrogen is from the downstream process.
Figure 6B:
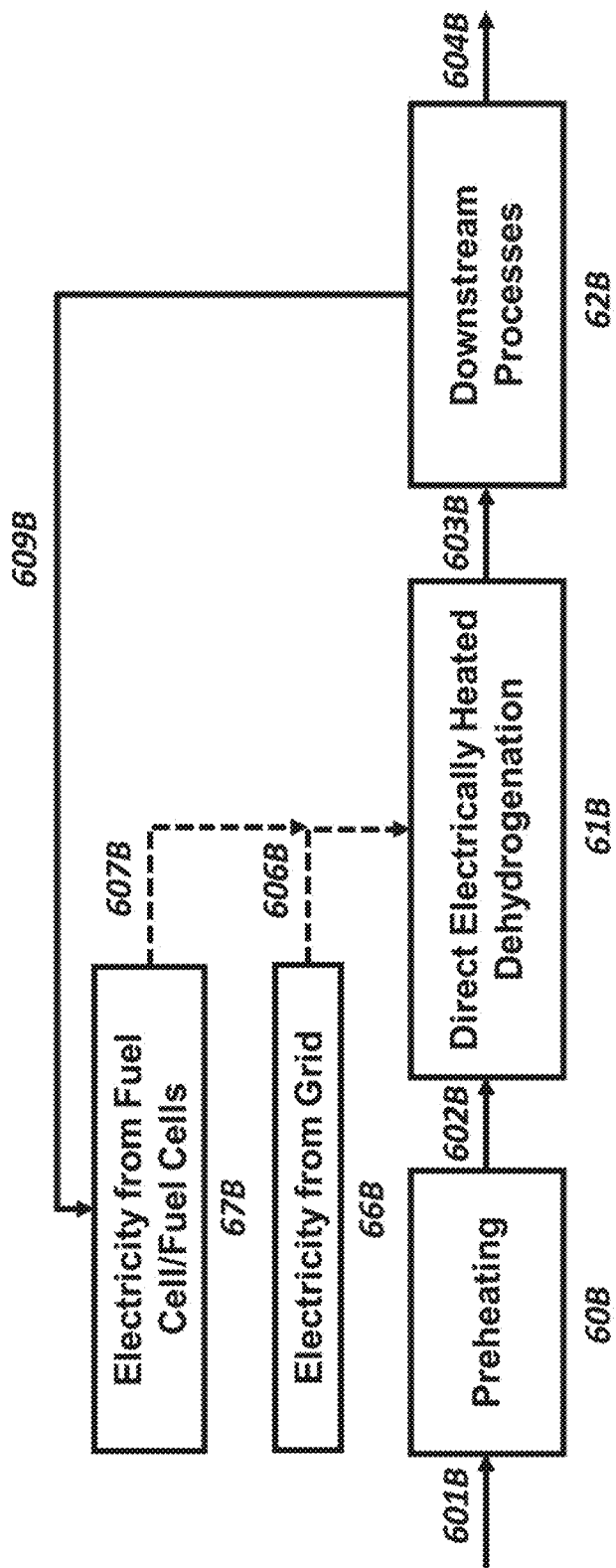
FIG. 6B is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from both grid and a hydrogen fuel cell or hydrogen fuel cells wherein the hydrogen is from the downstream process.
Figure 6C:
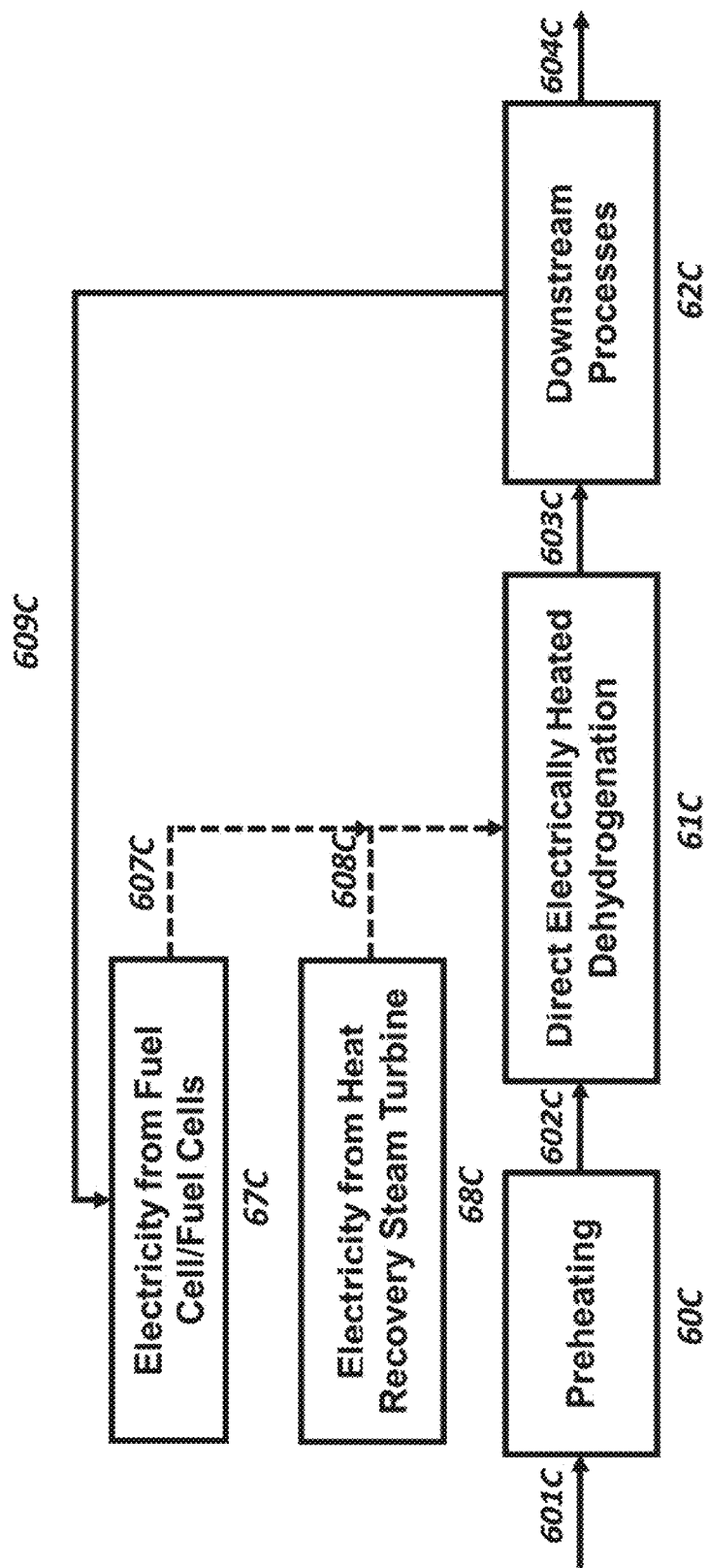
FIG. 6C is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from both a heat recovery steam turbine or heat recovery steam turbines and a hydrogen fuel cell or hydrogen fuel cells wherein the hydrogen is from the downstream process.
Figure 6D:
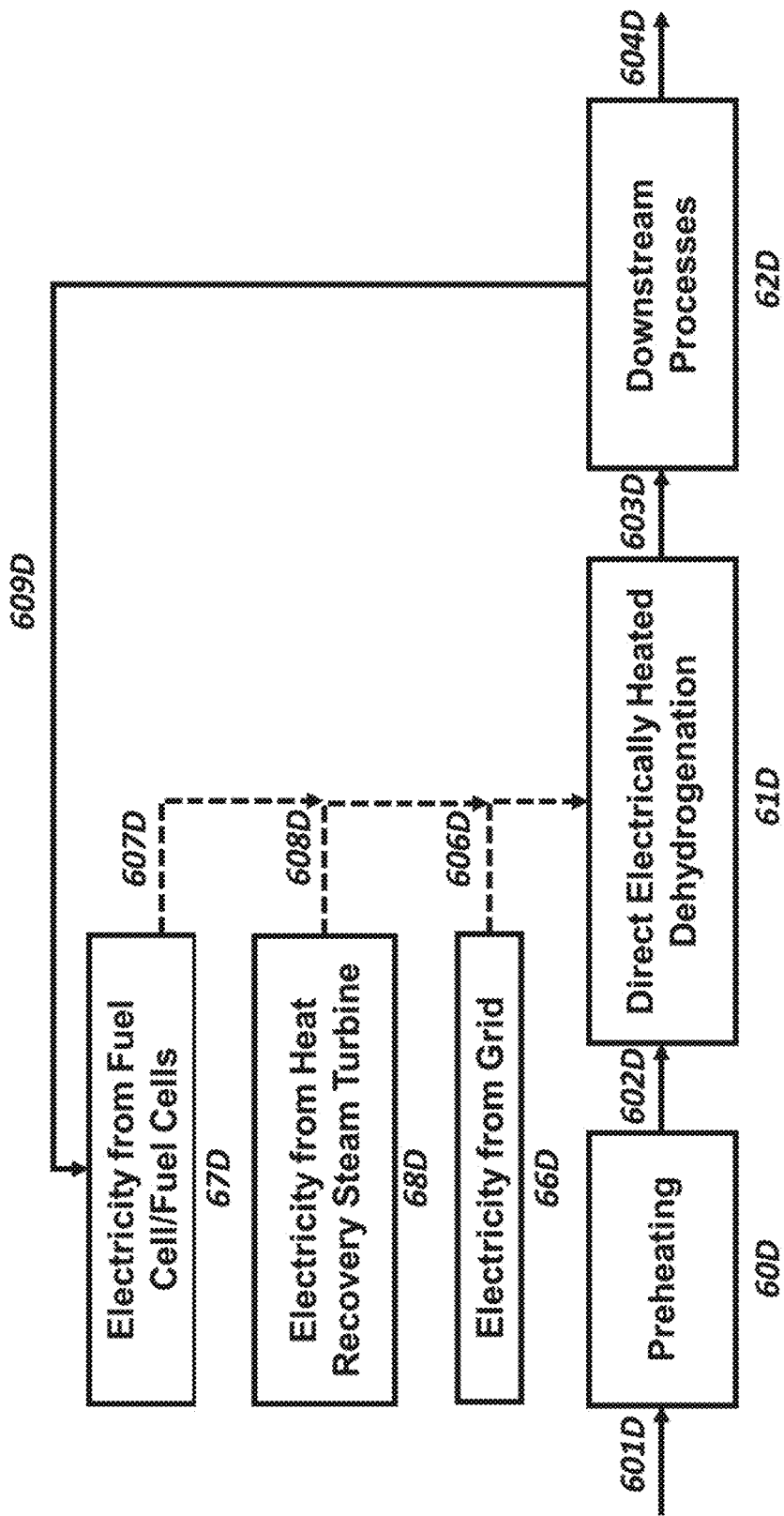
FIG. 6D is a block diagram of an illustrative process where a feed hydrocarbon mixture is preheated and fed to a direct electrically heated dehydrogenation reactor, the reactor exhaust stream is sent to the downstream processes. The needed electricity for the dehydrogenation reactor is from the grid, a heat recovery steam turbine or heat recovery steam turbines, and a hydrogen fuel cell or hydrogen fuel cells wherein the hydrogen is from the downstream process.

FIG. 6A-6D depict alternative embodiments where at least part of the electricity is from a fuel or fuel cells wherein $H_2$ from any downstream processes is used as the fuel. In FIG. 6A, for example, all the electricity for the direct electrically heated dehydrogenation reactor is from the fuel cell or fuel cells 67A and $H_2$ from the downstream processes 62A is used as the fuel. In FIG. 6B, the electricity for the direct electrically heated dehydrogenation reactor is from the grid 66B and the fuel cell or fuel cells 67B and the $H_2$ from downstream processes 62B is used as the fuel. In FIG. 6C, the electricity for the direct electrically heated dehydrogenation reactor is from the steam power cycle 68C and the fuel cell or fuel cells 67C and the $H_2$ from downstream processes 62C is used as the fuel. In FIG. 6D, the electricity for the direct electrically heated dehydrogenation reactor 61D is from the grid 66D, steam power cycle 68D and the fuel cell or fuel cells 67D and the $H_2$ from downstream processes 62D is used as the fuel.

Figure 7A:
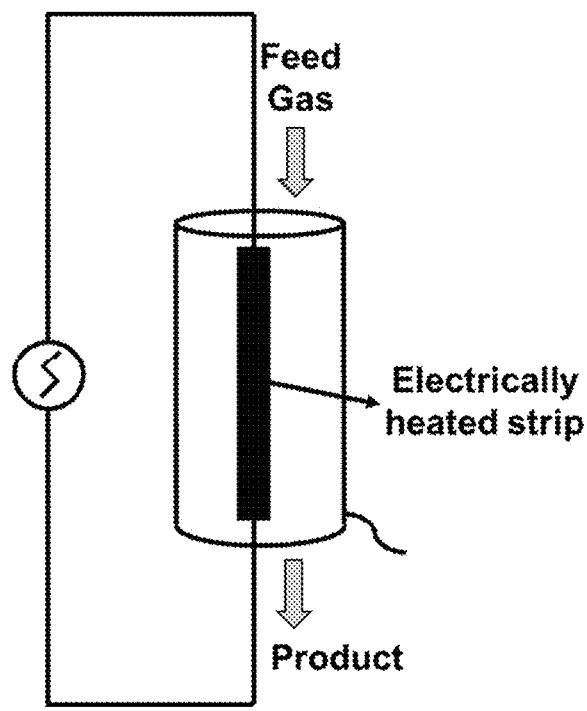
FIG. 7A depicts an illustrative detailed design of a tube dehydrogenation reactor wherein a heating element strip is heated inside the reactor tube by applying voltage across its two ends.

The processes provided herein do not include conventional electrical furnaces that radiantly heat the reactor tubes from electrical resistances located outside the tubes. In these furnaces, the outer surface of the reactor tube is heated by the electrical resistances in the furnace. The heat then conducts through the metal walls to the inside surface of the tube and then eventually through convection to the inflowing gaseous reactant stream. Such a flow of heat from the electrically resistive wires to the outside of the tube and then through the tube wall to the inflowing gaseous reactant stream is slow and inefficient. The tube walls are thick and build large temperature gradients leading to challenges associated with tube metallurgy. As explained herein, the heat is directly transferred from the heating element to the gaseous reactant stream as shown in FIG. 7A. A heating element made of resistive metal strip capable of providing high temperatures up to 800° C. to 900° C. can be placed inside a container, which in FIG. 7A is a cylindrical reactor tube. The gaseous reactant stream enters at one end of the tube and is heated rapidly by directly coming in contact with the heated metal strip. The metal strip can be heated by applying electrical voltage across it. The amount of energy transferred to the gaseous reactant stream can be controlled through the flow of electrical current through the metal strip. The dehydrogenation reaction can be conducted inside the tube and the gaseous stream can exit at the product end of the tube for further downstream processing. The direct heating of the gaseous reactant stream allows rapid transfer of heat to the stream and reaction is conducted rapidly. This allows for relatively smaller size of the reactor tube. Since heat does not flow across the thickness of tube wall to heat the gaseous reactant stream, its temperature can be lower and it is possible to construct thicker tubes for dehydrogenation reactions conducted at pressures much higher than the atmospheric pressure. The heating elements can be any suitable alloy which are electrically resistive, can provide desired temperature, up to 800° C. to 900° C. under the application of electric voltage difference across its two ends, and is stable in the environment of gaseous reactant stream and its products formed during dehydrogenation. Some examples include Fe—Cr—Al and Fe—Cr—Ni alloys and other combinations thereof.

Figure 7B:
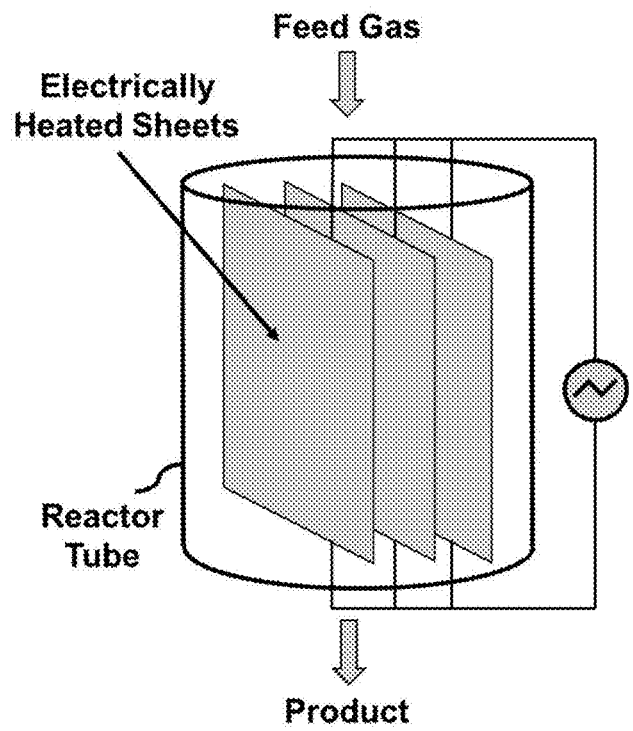
FIG. 7B depicts an illustrative detailed design of parallel sheets of the heating elements used inside the dehydrogenation reactor tube.
Figure 7C:
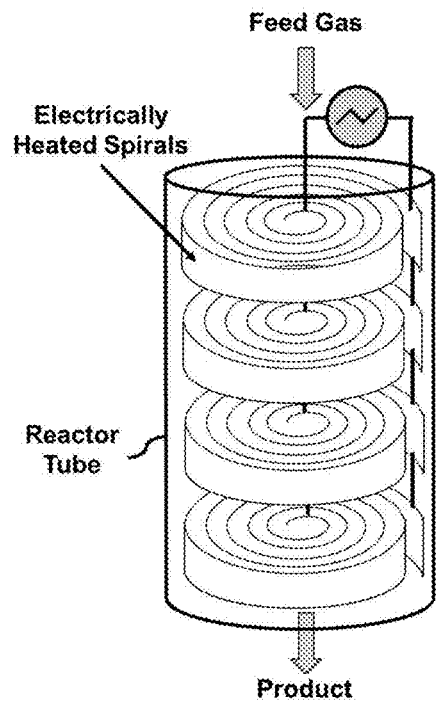
FIG. 7C depicts an illustrative detailed design of spiral wounds of the heating element used inside the dehydrogenation reactor tube.
Figure 7D:
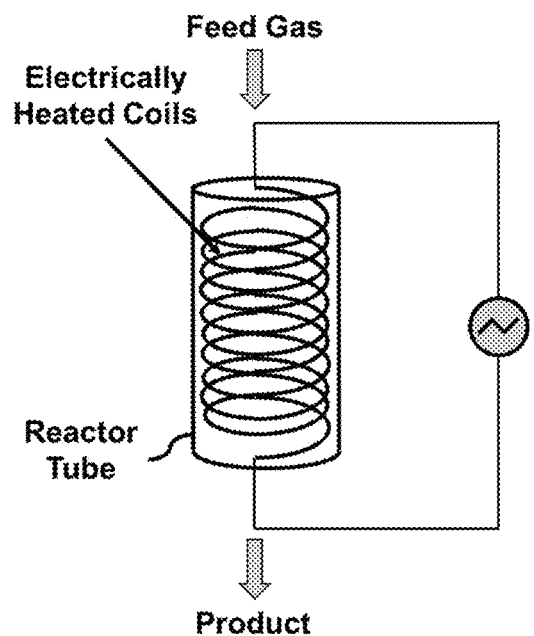
FIG. 7D depicts an illustrative detailed design of a tube reactor utilizing internally located electrically heating coils.
Figure 7E:
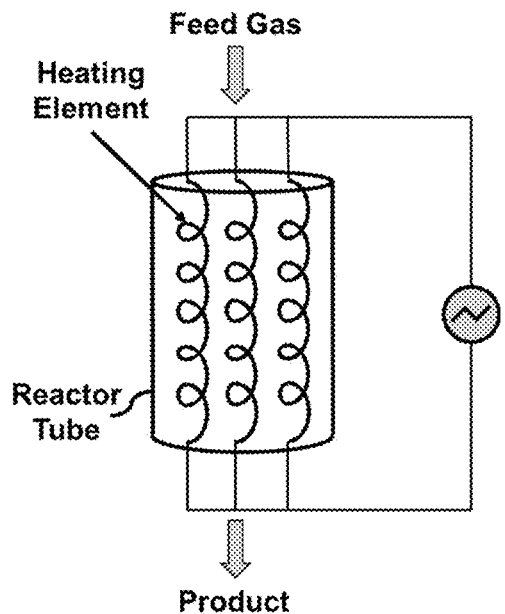
FIG. 7E depicts an illustrative detailed design of a tube reactor utilizing multiple wires of the heating element enclosed in a reactor tube.
Figure 7F:
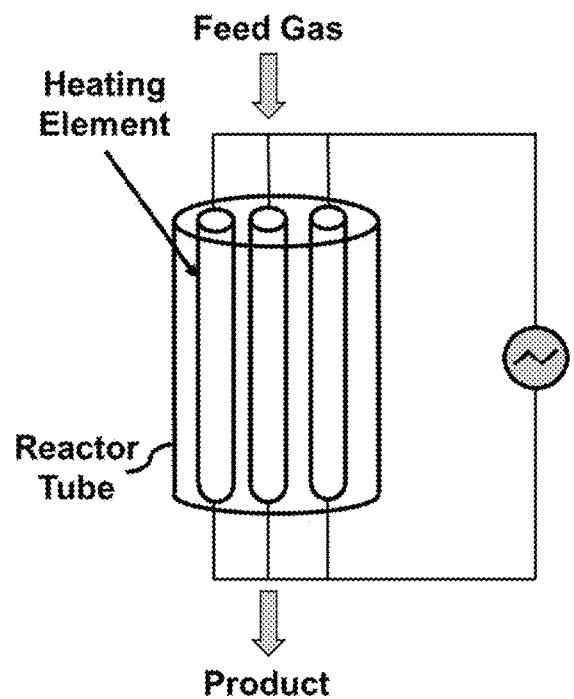
FIG. 7F depicts an illustrative detailed design of a tube reactor with heating elements that are thin tubes and enclosed within a high pressure reactor tube.

While FIG. 7A shows a single heating element in the form of a strip enclosed in a container in the form of a reactor tube, any suitable geometrical arrangement of the heating element and the container may be used in the process of the current invention. Especially the geometric arrangements that enhance the contact between the heating element and the flowing gaseous reactant stream to enhance direct heat transfer for rapid and efficient heating are preferred. The gaseous reactant stream is heated and dehydrogenated within a few seconds and preferably within a second and most preferably within hundreds of milliseconds. Some examples are illustrated in FIGS. 7B, through 7F. In FIG. 7B, the heating element consist of several parallel resistive alloy sheets enclosed within the reactor tube. The spacing between the parallel sheets is controlled for rapid heating of the gas flowing through this spacing, electrical voltage is applied across each of the parallel is shown. In FIG. 7C, the heating element strip is wound in the form of a spiral and voltage difference is applied between the two ends of the strip. A suitable insulating spacer allowing gaseous flow may be used as the heating element strip is wound in the form of a spiral. While single spiral wound element can be used to conduct the reaction, in FIG. 7C we show multiple spiral wounds connected in series for increased heat load. FIG. 7D shows the heating element wire in the form of a spiral. FIG. 7E demonstrates the use of multiple wires of the heating element enclosed in a reactor tube. In FIG. 7F, the heating elements are thin tubes which are enclosed within a high pressure reactor tube. One or more thin tubes of the heating elements are used.

Figure 7G:
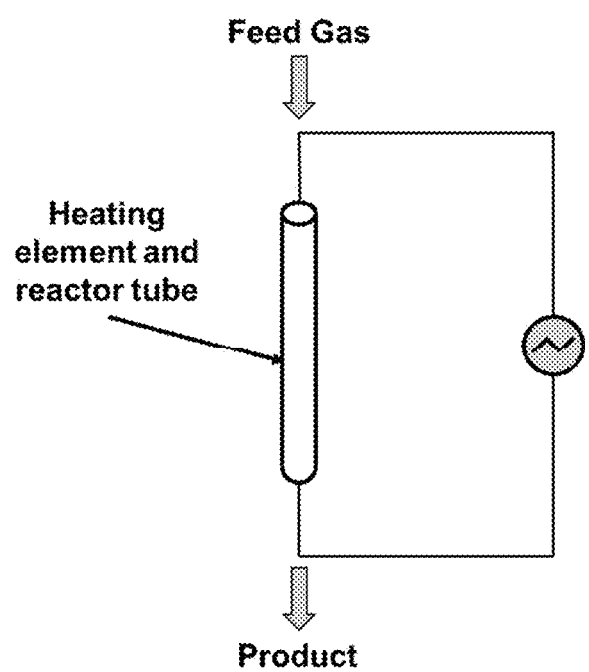
FIG. 7G depicts an illustrative detailed design of a tube reactor utilizing a heating element that is used to construct the reactor tube.

In another embodiment, the heating element may be used to construct the reactor tube. FIG. 7G shows such an arrangement. Due to requirement for high resistance, the tube wall of such a reactor will be quite thin and can be of the order of one millimeter or less. This will force to conduct the dehydrogenation reactor at close to atmospheric pressure as pressure difference between the inside and outside of the reactor tube will have to be necessarily small. As such this arrangement will be less preferred when compared to the type of arrangements demonstrated in FIGS. 7A through 7F. A benefit of the current process is that for the shale gas hydrocarbon mixture consisting of methane, ethane, propane, butane etc., the dehydrogenation temperature used are in the range of 750° C. to 900° C., and heating element alloys can be directly used without any catalyst coating on the surface. However, if needed, the surfaces of the heating element may be coated with a material to suppress coking and side reactions during dehydrogenation. When gases such as propane or butane is to be dehydrogenated, much lower temperatures in the range 500° C. to 650° C. along with a suitable catalyst are used. For such dehydrogenation cases where catalysts are desired, the heating element may be coated with a thin layer of catalyst. The coating thickness can range from a few micrometers to up to 200 micrometers.

Embodiments of the present invention provide a portable solution, in the field, as an alternative to a pipeline or flaring. As explained above, the electric power can be provided to a reactor at the well site. The reactor can be operated using the electric power on site or can be provided by a portable, gasoline or diesel powered, generator. The reactor and any desired separators also can be situated on a truck bed and driven to a location, allowing for dehydrogenation on an as needed or where needed basis, especially when the project economics do not justify the expense for a pipeline. Embodiments provided herein further provide an alternative to flaring a gas cap or shut-in well when re-entered for testing, workovers, etc.

For a small size hydrocarbon dehydrogenation process, the directly electrically heated reactors provide a compact, simple, and easy to operate alternative compared to current methods of using furnaces. Furthermore, as demonstrated through the following simulations, they also surprisingly provide an energy efficient alternative.

Prophetic Examples

Figure 4:
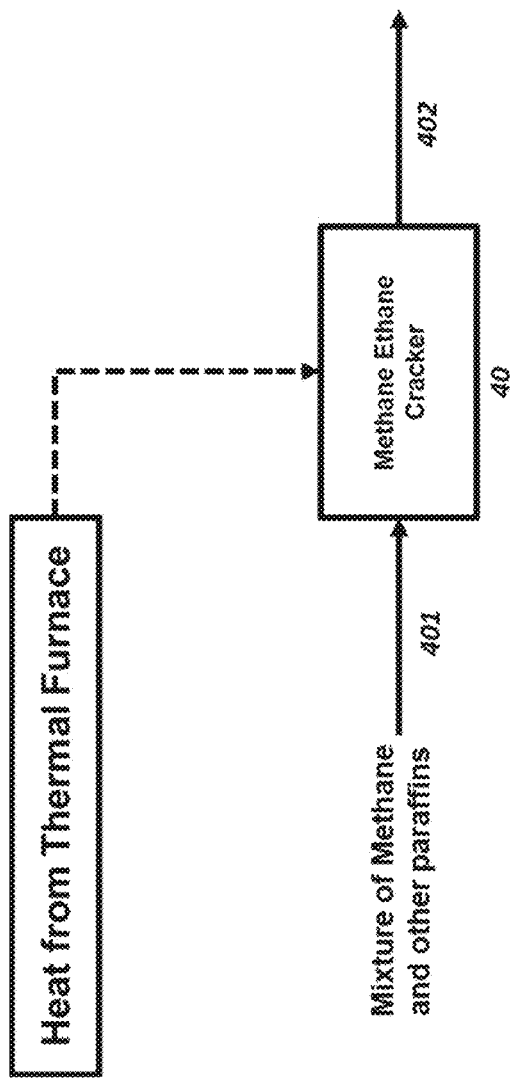
FIG. 4 is a block diagram illustrating another conventional process wherein a mixture of methane and other paraffins is sent to a methane ethane cracker without frontend separations.

The foregoing discussion can be further described with reference to the following non-limiting prophetic examples. Process simulation results are provided for the processes described above with reference to FIGS. 4, 5B and 6B. The process simulations were implemented by Aspen Plus. The feed information, including composition, temperature, and pressure, is from the typical shale gas stream from Bakken, which is shown in Table 1. A typical feed flowrate at the gathering station, 10 MMSCFD is assumed for all three simulations. All the reactions in the dehydrogenation reactors (Unit 40 in FIG. 4, Unit 51B, in FIG. 5B, Unit 61B in FIG. 6B) of all three processes were set at 90% of the equilibrium value. Besides major reactions, some key side reactions such as propane cracking into methane and ethylene are also set to be 90% of the equilibrium conversion. A pressure drop of 0.21 bar is assumed for all the unit operations. The downstream processes can be one or more separation steps to separate the mixture out of the dehydrogenation reactor into pure product streams. It is worth noticing that for the process depicted in FIG. 4, the $H_2$ produced can either be shipped as final product or used as a fuel in the furnace. So two simulations are made for this process, which are denoted as Simulation 1 and Simulation 2. The simulation for the process depicted in FIG. 5B is denoted as Simulation 3 and the simulation for the process depicted in FIG. 6B is denoted as Simulation 4.

The key energy consumption information of these four simulations is summarized in Table 2 below. For all four simulations, the energy needed for the dehydrogenation reactor is 12.2 MW or about $1\times10^5$ MJ to process 1 MMSCF of shale gas. However, depending on different ways to supply heat to the reactor, the final fuel consumption is different. In process Simulations #1 and #2 (FIG. 4), with methane or methane-$H_2$ fired furnace, due to small size of the plant, only heat in the radiant section is utilized for dehydrogenation. Expensive furnace designs to recover heat from the hot flue gas exiting the radiant section is not employed due to cost consideration for the associated equipment and handling of water and steam. In simulation #1, the furnace heat is with $CH_4$ as the fuel and the fuel consumption is 147 kmol/hr. In this case, $H_2$ from the dehydrogenation reaction is a byproduct. Another simulation with $H_2$ as a byproduct is simulation #3 (representative of FIG. 5B) wherein the dehydrogenation is operated with electricity from grid. The grid electricity is assumed to be generated from a combined-cycle gas-fired plants with 50% efficiency. The $CH_4$ consumption in this case is 109 kmol/hr, which is only 74% of the $CH_4$ consumed in simulation #1. Moreover, the entire furnace in simulation #1 is replaced by heating elements inside the reactor in simulation #3, which dramatically simplifies the reactor design. Simulations #2 and #4 are two simulations wherein $H_2$ produced in the dehydrogenation reaction process is used locally as a fuel. In simulation #2, the $H_2$ is blended with $CH_4$ and the combined stream is fed to the furnace. In this case, all the $H_2$ produced in simulation #2, 173 kmol/hr, and a portion of $CH_4$, 78 kmol/hr, are burned.

In simulation #4 (representative of FIG. 6B), hydrogen is fed to a fuel cell to generate a portion of the electricity and the rest of the electricity is from the grid. All the hydrogen generated in the process, 173 kmol/hr, is fed to the fuel cell to generate electricity. The rest of the electricity needed requires the combustion of 48 kmol/hr $CH_4$ in a combined-cycle gas-fired plants with 50% efficiency. The $CH_4$ consumption in simulation #4 is only 62% of that in simulation #2 for the process with a combustion furnace. The process represented by simulation #4 is not only more energy efficient but simpler to build and operate.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for dehydrogenating natural gas liquids (NGLs), comprising:
   providing a hydrocarbon feed stream comprising one or more natural gas liquids (NGLs) $C_{2+}$; and
   dehydrogenating at least a portion of the one or more natural gas liquids (NGLs) into one or more $C_{2+}$ olefinic hydrocarbons within an electrically heated reactor.

2. The process of claim 1, wherein electrical energy for the electrically heated reactor comes from a power grid.

3. The process of claim 1, wherein electrical energy for the electrically heated reactor comes from one or more fuel cells.

4. The process of claim 3, wherein at least one of the one or more fuel cells is a hydrogen cell.

5. The process of claim 4, wherein hydrogen to the hydrogen fuel cell is one of the products from the dehydrogenation process.

TABLE 2

| key energy consumption information for the four simulations | | | | | |
|---|---|---|---|---|---|
| Simulation No. | Energy for dehydrogenation | Energy from fuel cell | Energy from grid | Energy from furnace | $H_2$ consumption | $CH_4$ consumption |
| 1 | 12.2 MW | 0 | 0 | 12.2 MW | 0 | 147 kmol/hr |
| 2 | 12.2 MW | 0 | 0 | 12.2 MW | 173 kmol/hr | 78 kmol/hr |
| 3 | 12.2 MW | 0 | 12.2 MW | 0 | 0 | 109 kmol/hr |
| 4 | 12.2 MW | 6.9 MW | 5.3 MW | 0 | 173 kmo/hr | 48 kmol/hr |

6. The process of claim 1, wherein electrical energy for the electrically heated reactor comes from a power grid and one or more fuel cells.

7. The process of claim 1, wherein electrical energy for the electrically heated reactor comes from a power grid and one or more steam turbines that recover work from other heat streams in the process.

8. The process of claim 1, wherein electrical energy for the electrically heated reactor comes from one or more fuel cells and one or more steam turbines that recover work from heat streams in the process.

9. The process of claim 1, wherein electrical energy for the electrically heated reactor comes from a power grid, one or more steam turbines that recover work from heat streams in the process, and one or more fuel cells.

10. The process of claim 1 wherein the hydrocarbon feed stream is a sweet and dry shale gas mixture.

11. The process claim 1, wherein the flowrate of the hydrocarbon feed stream is equal to or less than 200 MMSCFD, less than 50 MMSCFD or less than 20 MMSCFD.

12. The process of claim 1, wherein electrical energy for the electrically heated reactor is provided from one or more power grids, solar panels, windmills, hydropower, nuclear power, fuel cells, gas turbines, steam turbines, portable generators or combinations thereof.

13. The process of claim 1, wherein the hydrocarbon feed stream consists essentially of one or more natural gas liquids (NGLs).

14. The process of claim 1, further comprising:
obtaining a raw shale gas from a downhole formation;
separating methane from the raw shale gas to provide the hydrocarbon feed stream comprising one or more natural gas liquids (NGLs).

15. The process of claim 1, further comprising:
obtaining a raw natural gas from a downhole formation;
separating methane from the raw natural gas to provide the hydrocarbon feed stream comprising one or more natural gas liquids (NGLs).

16. A process for alkane dehydrogenation, comprising:
providing a hydrocarbon feed stream comprising one or more alkanes that are $C_{2+}$ hydrocarbons; and
dehydrogenating at least a portion of the one or more alkanes that are C2+ hydrocarbons into one or more $C_{2+}$ olefinic hydrocarbons within an electrically heated reactor, wherein the electrically heated reactor is a tube reactor comprising one or more internally located electrically heated elements to provide direct heat transfer from the heated element to the hydrocarbon feed stream.

17. The process of claim 16, wherein the heating element is a metal alloy strip.

18. The process of claim 16, wherein the tube reactor comprises one or more parallel sheets as heating elements.

19. The process of claim 16, wherein the tube reactor comprises one or more spiral wounds.

20. The process of claim 16, wherein multiple wires of the heating element are enclosed in the reactor tube.

21. The process of claim 16, wherein the heating elements are thin tubes and are enclosed within the tube reactor.

22. The process of claim 16, wherein the tube reactor is a heating element.

23. The process of claim 16, wherein the heating element is an alloy comprising any combination of Fe, Cr, Ni, and Al.

* * * * *